(12) United States Patent
Kanomata et al.

(10) Patent No.: US 6,307,204 B1
(45) Date of Patent: *Oct. 23, 2001

(54) UV DETECTOR FOR LIQUID CHROMATOGRAPHY

(75) Inventors: Takeshi Kanomata; Shinichi Kikuchi; Mitsunori Sakamoto, all of Hachioji (JP)

(73) Assignee: Jasco Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/240,802

(22) Filed: Jan. 28, 1999

Related U.S. Application Data

(63) Continuation-in-part of application No. 09/188,928, filed on Nov. 9, 1998, now Pat. No. 6,118,536.

(30) Foreign Application Priority Data

Nov. 14, 1997 (JP) .................................................. 9-329658
Feb. 5, 1998 (JP) ................................................ 10-037935
Jul. 7, 1998 (JP) ................................................ 10-205821

(51) Int. Cl.$^7$ ..................................................... G01J 1/42
(52) U.S. Cl. ............................................................. 250/373
(58) Field of Search .............................. 250/373; 210/656

(56) References Cited

U.S. PATENT DOCUMENTS

| | | | |
|---|---|---|---|
| 3,666,941 | * 5/1972 | Watson | 250/365 |
| 4,011,451 | 3/1977 | Nelson | 250/343 |
| 4,067,653 | * 1/1978 | Fletcher et al. | 356/433 |
| 5,153,679 | * 10/1992 | Gilby | 356/440 |
| 5,642,625 | * 7/1997 | Cates, Jr. et al. | 62/55.5 |
| 5,883,721 | * 3/1999 | Gilby et al. | 356/440 |
| 6,118,536 | * 9/2000 | Sakamoto et al. | 356/364 |

* cited by examiner

Primary Examiner—Seungsook Ham
Assistant Examiner—Shun Lee
(74) Attorney, Agent, or Firm—Marger Johnson & McCollom, P.C.

(57) ABSTRACT

A UV detector for liquid chromatography is equipped with a light source; a flow cell having a light entrance side and a light exit side; a first optical system for shining light from the light source into the flow cell so as to form an image roughly at the light exit side of the flow cell or at a position outside the flow cell at a prescribed distance away from the light exit side thereof; a light detector; a second optical system for directing light exiting the flow cell to the light detector; and a truncated cone shaped sample chamber formed in the flow cell along the axial direction thereof, with the base of the truncated cone being positioned at the light entrance side of the flow cell.

3 Claims, 16 Drawing Sheets

UV DETECTOR FOR LIQUID CHROMATOGRAPHY

This application is a continuation-in-part of Ser. No. 09/188,928, filed Nov. 9, 1998, now U.S. Pat. No. 6,118,536, commonly-assigned herewith.

BACKGROUND OF THE INVENTION

1. Field of the Invention

The present invention relates to an UV detector for liquid chromatography, and in particular relates to an improved flow cell structure.

2. Description of the Related Art

FIG. 1 shows an example of a prior art multiple wavelength detector used in liquid chromatography, in which light emitted from a light source 1 is converged by a converging system (represented by one lens in FIG. 1) 2 and shines into a flow cell 3. As shown in FIG. 2, the flow cell 3 is constructed from a cylindrical sample chamber 6 sandwiched between window 4, 4 made of a transparent material such as quartz or the like, and the light which shines into the flow cell 3 from the light source 1 enters the sample chamber 6 while a solvent flows therethrough. Then, as the light passes through the sample chamber 6, some of it is absorbed by the sample contained in the solvent.

The light which exits the flow cell 3 is dispersed by a light dispersing optical system (represented by one diffraction grating in FIG. 1) 7 and shines onto a photodiode array of a light detector 8 which converts each wavelength light intensity into electrical signals to obtain data about the light which passes through the flow cell 3.

In this connection, when the flow cell shown in FIG. 2 is used in a multiple wavelength detector for liquid chromatography, the following problem occurs.

Namely, the light shining into the flow cell has a poor utilization efficiency. This is due to the fact that the light from the light source 1 generally enter the flow cell at some solid angle. Accordingly, a portion of the light entering the flow cell 3 strikes the inner cylindrical walls and is absorbed, and because this portion of light does not pass through the flow cell 3, the utilization efficiency of the light entering the flow cell 3 is reduced. As a result, the detection signals (electrical signals) outputted from the light detector 8 (photodiode array) are weakened, and this causes an increase in the noise of the measured data.

One example proposal in the prior art for overcoming the problem described above is an invention disclosed in Japanese Laid-Open Patent Application No. HEI-8-3483. The solution proposed in HEI-8-3483 involves giving the sample chamber 6 a truncated cone shape which expands in the direction of travel of the light, as shown in FIG. 3. When the sample chamber 6 is given such a shape, the light which enters the flow cell 3 will not be absorbed because such light will not strike the inner wall surface of the sample chamber 6 even if the light enters at some solid angle. In this connection, Japanese Laid-Open Patent Application No. SHO-54-33871 and Japanese Laid-Open Utility Model Application No. SHO-40-14080 are publications which have a different object than that of the present invention but disclose a sample chamber having a truncated cone shape which expands in the direction of travel of the light like that described above.

However, if the sample chamber 6 has a shape like that shown in FIG. 3, the following problem occurs. Namely, even when the light absorbance is the same, if the solvent is replaced with another solvent having a different index of refraction, the output of the light detector 8 will change, and this will cause a change in the base line of the measured data. The cause of such change is believed to be as follows. Namely, when a new solvent having an index of refraction different from that of the solvent flowing up to the current moment is flowed into the flow cell 3, the portion of the solvent roughly near the center of the sample chamber 6 has a fast flow rate, and this gives the portion of the new solvent in the center of the sample chamber 6 a higher density than that of the portion near the inner walls of the sample chamber 6. Now, because this creates an effect like that of a lens (known as the "lens effect"), the light entering the flow cell 3 is refracted, and a portion of such refracted light strikes the inner walls of the sample chamber 6 and is absorbed. As a result, the output of the light detector 8 will change, and this will cause the above-described change in the base line of the measured data.

Further, the spectrophotometer disclosed in Laid-Open Patent Application No. HEI-2-259452 is similar in structure to the present invention. Looking solely at the flow cell structure, the invention disclosed in the HEI-2-259452 has a sample chamber formed with an expanded inner shape at the light entrance side. However, in this published invention, a slit must be arranged between the flow cell and the light source, and the light forms an image near the slit at a position away from the light entrance side of the flow cell.

When such structure is used, the light emitted from the light source enters the flow cell after being constricted by the slit, and the portion of the light traveling to the outside is reflected by the inner surface of the sample chamber and does not reach the photosensor. In other words, the elements are arranged so that the photosensor receives only the portion of light that is roughly paraxial to a light path not affected for the most part by changes in the internal conditions of the flow cell, such as changing the solvent or the like. Consequently, there is a loss in sensitivity due to the reduction in the amount of light that is received and used for measurements.

SUMMARY OF THE INVENTION

In consideration of the background presented above, it is an object of the present invention to solve the problems of the prior art described above by providing a UV detector for liquid chromatography which makes it possible to increase the utilization efficiency of the light entering the flow cell, and reduce changes in the base line even in the case where the index of refraction of the solvent flowing through the flow cell has changed.

In order to achieve the object stated above, the UV detector for liquid chromatography according to the present invention is equipped with a light source; a flow cell having a light entrance side and a light exit side; a first optical system for shining light from the light source into the flow cell so as to form an image roughly at the light exit side of the flow cell or at a position outside the flow cell at a prescribed distance away from the light exit side thereof; a light detector, a second optical system for directing light exiting the flow cell to the light detector; and a truncated cone shaped sample chamber formed in the flow cell along the axial direction thereof, with the base of the truncated cone being positioned at the light entrance side of the flow cell. Further, by providing the second optical system with a diffraction element, the UV detector for liquid chromatography according to the present invention can be used to carry out multiple wavelength measurements having significantly better results than those obtained with prior art wavelength detectors. Of course, it is also possible to apply the present invention to a type of detector having a diffraction element provided in the first optical system.

Now, as described above, because the base of the truncated cone shaped sample chamber is arranged at the light entrance side of the flow cell, the part of the sample chamber having the larger diameter is positioned at the light entrance side of the flow cell to face the incident light. Thus, the part of the sample chamber having the smaller diameter is positioned at the light exit end of the flow cell. In this connection, regardless of how small the narrow end (i.e., the narrower part of the truncated cone) of the sample chamber is, such narrow end will have a non-zero diameter, and for this reason, the term "truncated cone" is used instead of "cone".

Now, in the case where a solvent having a different index of refraction than the solvent currently flowing through the flow cell is flowed in, the change in the index of refraction will cause the position of the light entrance of the flow cell to change when viewed from the diffraction element. However, because the position of the light exit of the flow cell is mechanically fixed, the position of an image formed on the light detector does not change. Accordingly, the base line changes that occur when a new solvent having a different index of refraction is introduced into the flow cell can be significantly reduced.

Further, the light entering the flow cell has a focal point roughly at the light exit side of the flow cell, and by making the solid angle of the truncated cone larger than the solid angle of the incident light, it is possible to prevent energy losses due to light striking the inner wall surfaces of the sample chamber (i.e., all the light reaches the light exit of the flow cell). Accordingly, the image of the light exit of the flow cell can be formed on the light detector (e.g., a photodiode array) without the loss of energy.

Further, as shown in the drawings of the preferred embodiments, by providing a flow inlet path at the light exit side of the flow cell, the solvent (sample) can be made to flow from the light exit side of the flow cell toward the light entrance side thereof. In this arrangement, the solvent flowing through the center of the sample chamber spreads out due to the fact that the truncated cone shaped sample chamber expands from the flow inlet side of the flow cell to the flow outlet side thereof. In this way, the flow rate at the center of the flow cell is reduced, and this makes it possible to reduce the "lens effect" that occurs when the flow rate at the center is higher than the flow rate of the surrounding areas. Furthermore, this arrangement also makes it possible to reduce the changes that occur in the base line when a new solvent having a different index of refraction is introduced into the flow cell.

DETAILED DESCRIPTION OF THE PREFERRED EMBODIMENTS

Figure 4:
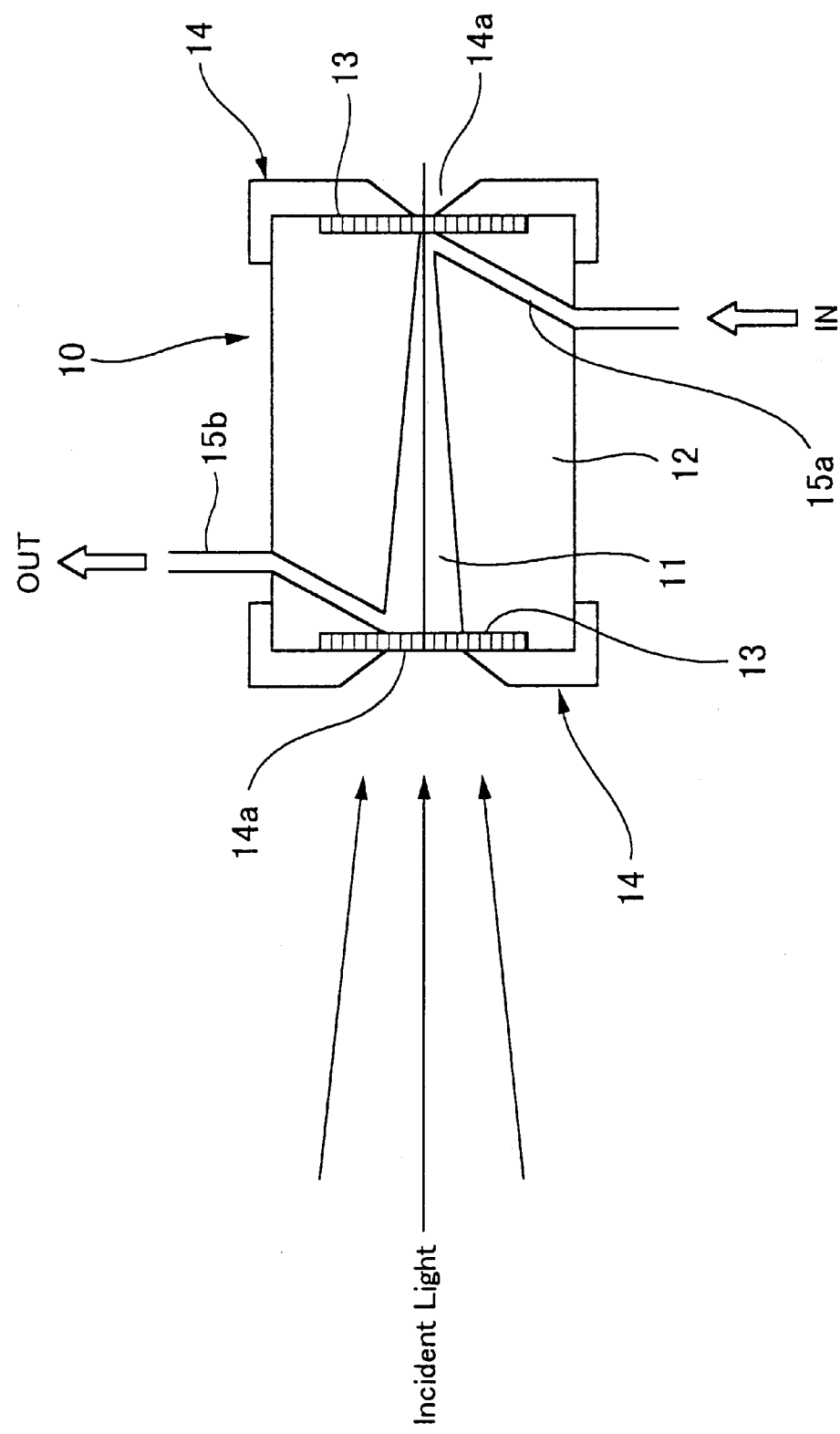
FIG. 4 is a cross-sectional view of one embodiment of a flow cell which forms an essential portion of the present invention.

FIG. 4 shows an example flow cell 10 which forms the essential portion of the present invention. As shown in the drawing, the flow cell 10 is constructed from a cylindrical flow cell block 12 provided with a sample chamber 11 which passes therethrough in the axial direction, and window 13, 13 made from transparent quartz glass or the like provided on either side of the flow cell block 12 in the axial direction. Although not shown in the drawing, a thin appropriately TEFLON® (polytetrafluoroethylene) sheet is provided between the window plates 13, 13 and the flow cell block 12 to ensure a liquid-tight seal, and by means of O-rings the windows 13, 13 are fixed with a tight seal to the flow cell block 12 by window flange 14, 14 each provided with an opening 14a.

In this arrangement, light enters the sample chamber 11 after passing through the opening 14a of the window flange 14 and the window 13 at the light entrance side of the flow cell 10, and then the light exits the flow cell 10 via the window 13 and opening 14a at the light exit side. Further, the flow cell block 12 is provided with a flow inlet path 15a and a flow outlet path 15b which extend in the radial direction near the axial ends thereof. In this way, the sample (solvent) flows into the sample chamber 11 from the flow inlet path 15a at the light exit side of the flow cell 10, and then after passing through the sample chamber 11 in the axial direction, the sample flows out of the flow cell 10 via the flow outlet path 15b at the light entrance side of the flow cell 10.

In the present invention, the inside of the sample chamber 11 is given a truncated cone shape which narrows in the direction toward the light exit side of the flow cell 10. Namely, when the flow cell 10 is arranged in a detector, the truncated cone shaped sample chamber 11 is positioned so that the bottom surface of the truncate cone (i.e., the larger diameter part is placed at the light entrance side. In this connection, FIG. 5 shows one embodiment of a multiple wavelength detector according to the present invention in which the flow cell 10 is arranged as described above.

Figure 5:
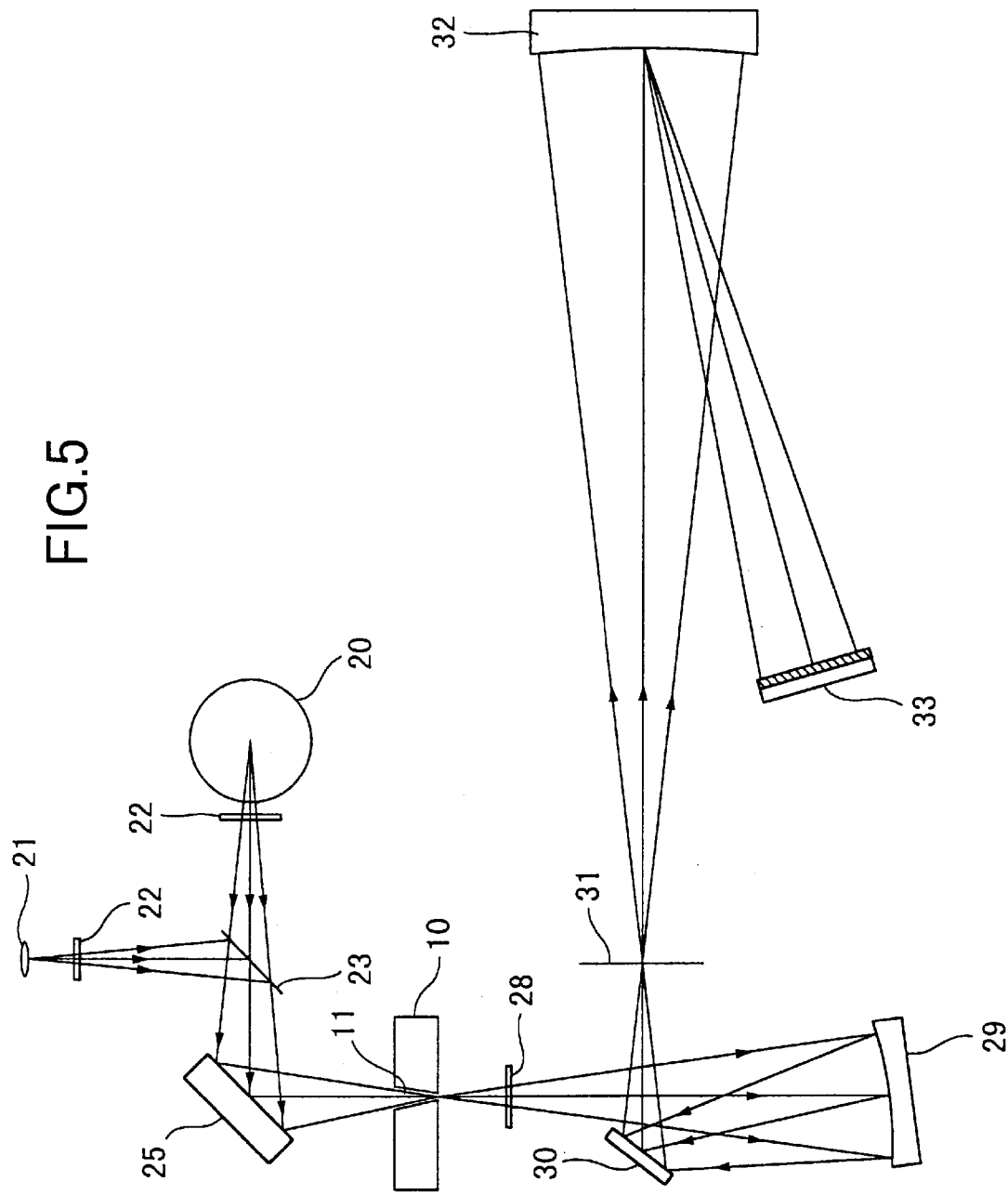
FIG. 5 is a schematic view of one embodiment of a detector according to the present invention.

As shown in FIG. 5, the multiple wavelength detector uses a deuterium lamp 20 and a tungsten lamp 21, and a window plate 22 formed with openings that enable prescribed wavelengths to pass therethrough is provided in front of the light emitting surface of each of the lamps 20, 21. Further, the lamps 20, 21 are positioned to have roughly orthogonal light-emission light paths, and arranged at the intersection of such orthogonal light paths is a half mirror 23. With this arrangement, the light from the deuterium lamp 20 and the light from the tungsten lamp 21 are combined in an appropriate proportion ratio and directed along a single light path.

Figure 6:
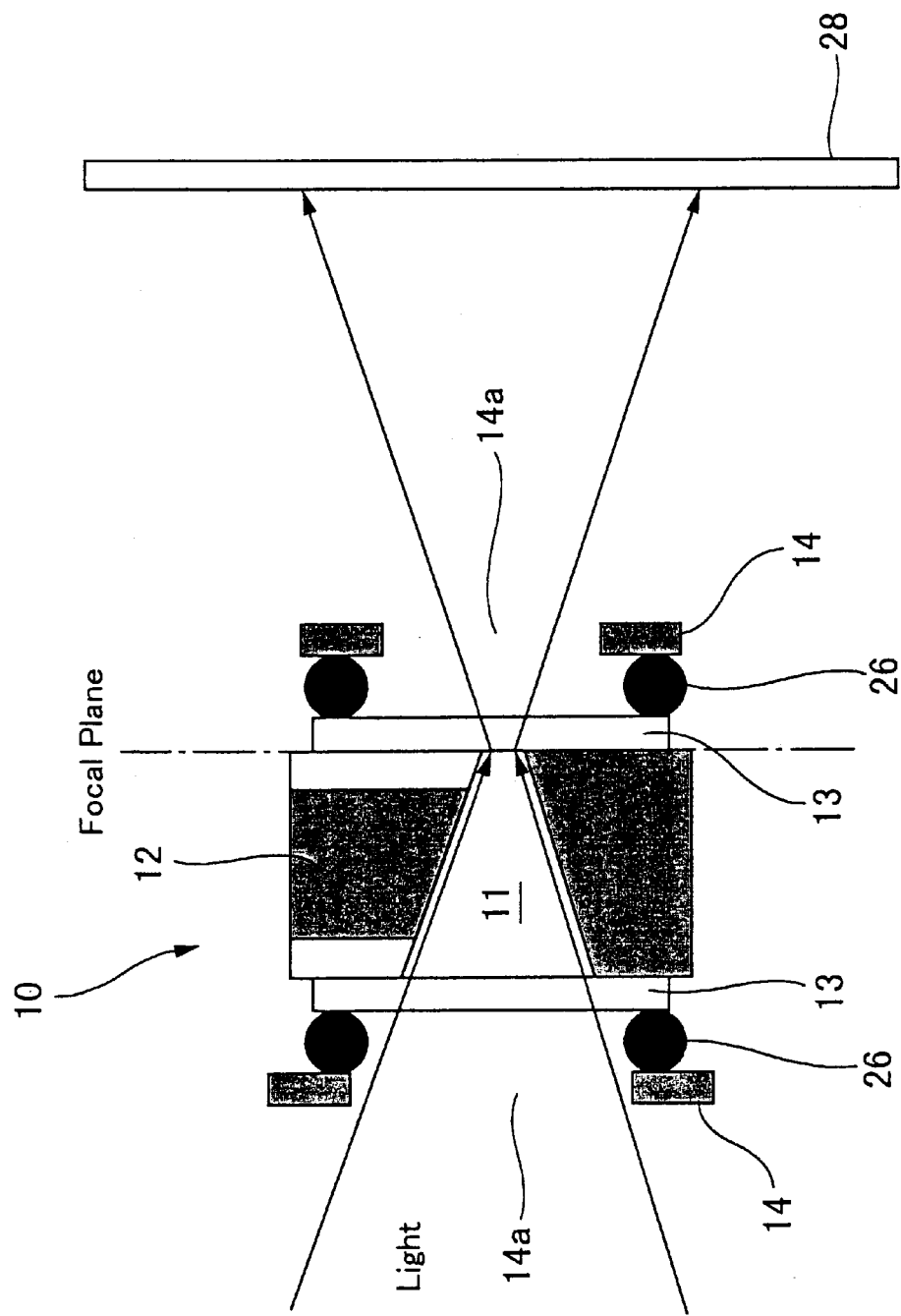
FIG. 6 is a cross-sectional outline view of the flow cell used in the present invention.

This combined light is then converted by an off-axis elliptical mirror 25 passes through the sample chamber 11 of the flow cell 10. Now, as described above, the flow cell 10 is positioned with the large diameter opening end of the sample chamber 11 arranged to face the off-axis elliptical mirror 25. Further, the converged light described above is adjusted to form an image at the output side of the flow cell 10 (i.e., at the place where the opening of the sample chamber has the smallest diameter). Here, it should be noted that an arrangement with this type of positional relationship forms the special feature of the present invention. In this connection, FIG. 6 is an enlarged view of a portion of the flow cell 10 shown in FIG. 4, in which the reference number 26 designates the provision of O-rings.

Next, the light that has passed through the flow cell 10 passes through a quartz window plate 28, (used to eliminate effects due to fluid leaking into the optical system adjacent the flow cell chamber), and then, after being reflected first by sphereical mirror 29 and then by the plate mirror 30, such light forms an image on an entrance slit 31 of the polychromator. Then, the light which passes through the entrance forms an image on a light detector (photodiode array: PDA) 33. Further, although not shown in the drawing, the light detector 33 outputs electrical signals corresponding to light intensity to a signal processing device which carries out prescribed signal processing operations based on such electrical signals.

Now, the reason for providing the window 28 is as follows. Namely, in the case where fluid leaks from the flow cell 10, if such leaking fluid or vapor therefrom flows into side where the polychromator is arranged, the diffraction grating 32 and the mirrors 29 and 30 will immediately be degraded. Thus, in order to prevent this problem from occurring, window plate 28 of quartz (which is stable with respect to the solvent) is provided to separate the flow cell 10 and the polychromator.

Figure 7:
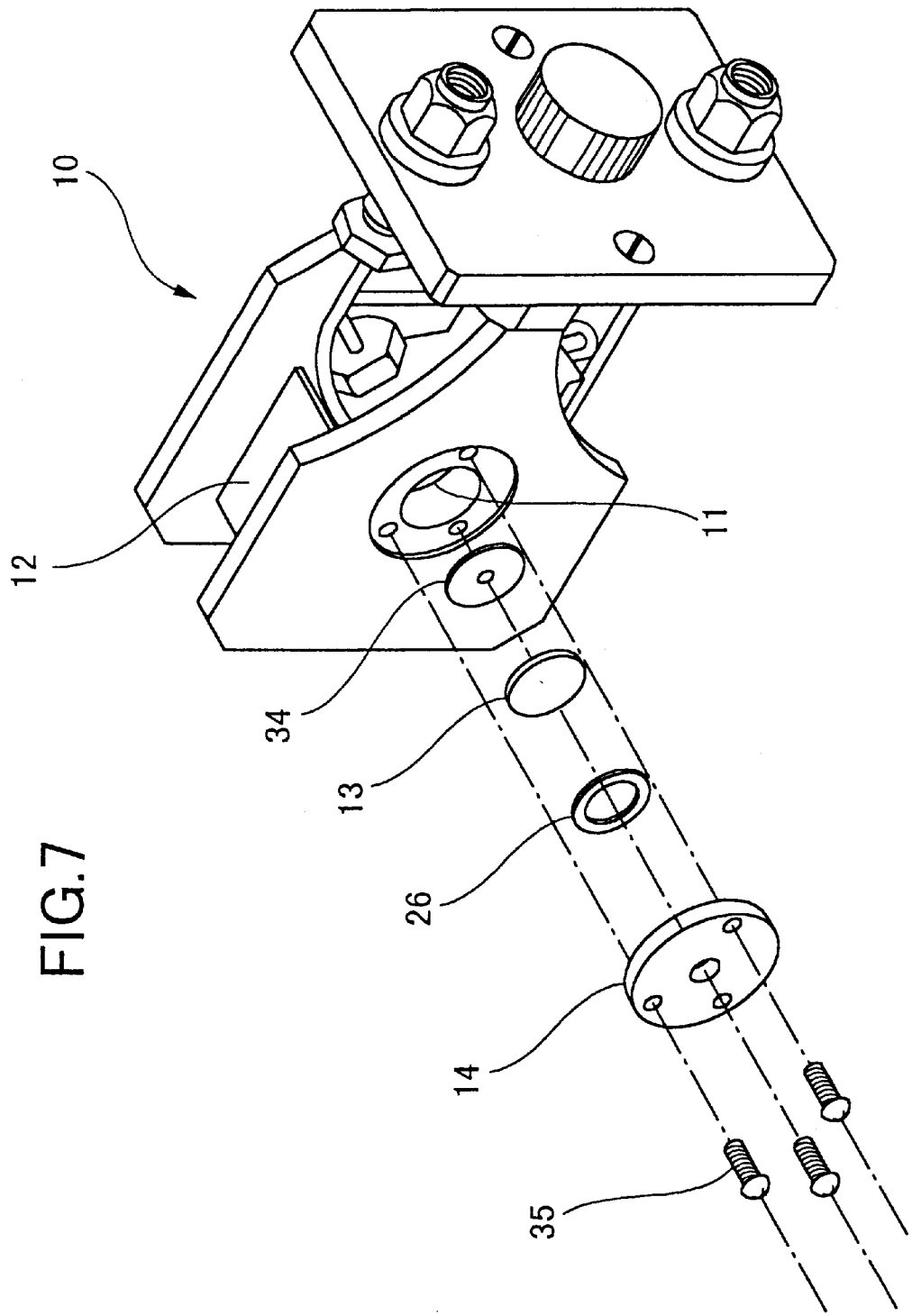
FIG. 7 is an exploded view showing the actual structure of one example of a flow cell according to the present invention.
Figure 8:
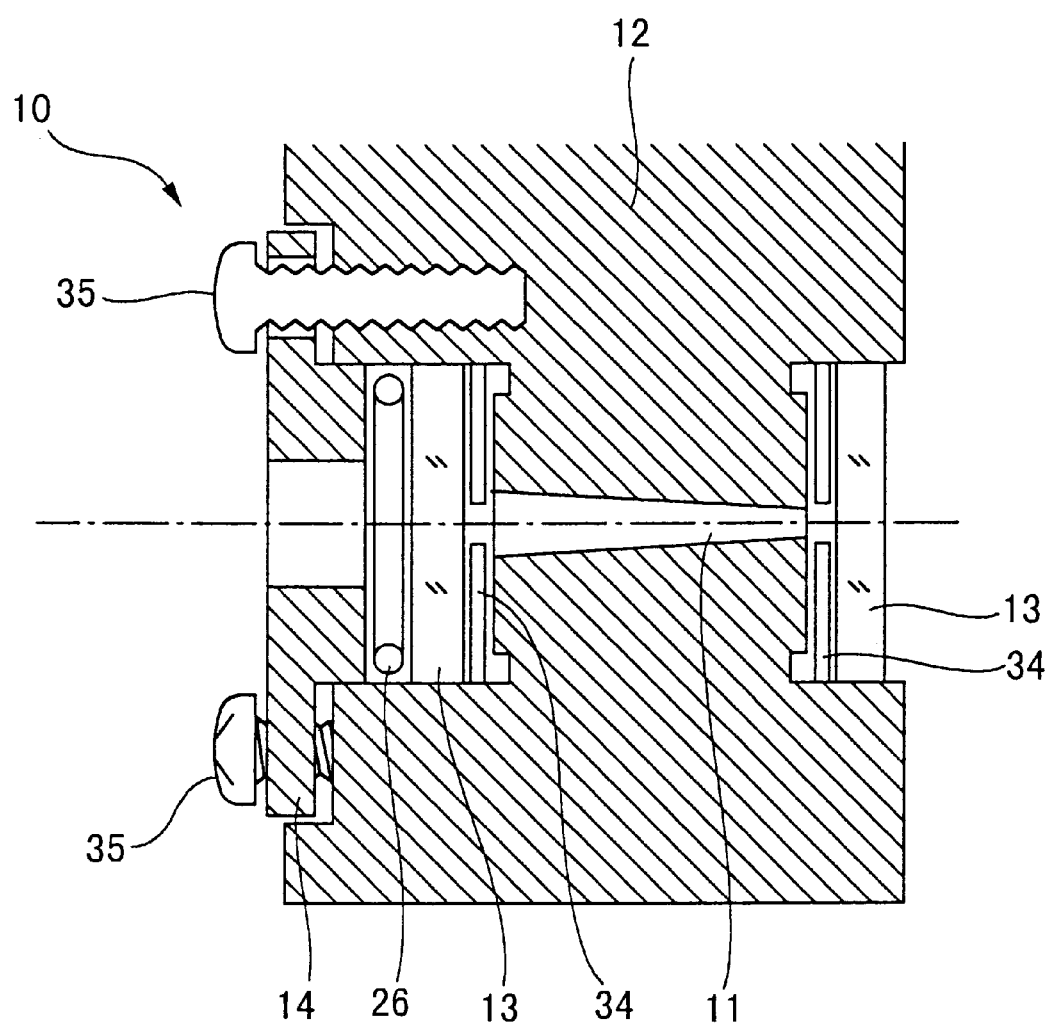
FIG. 8 is a cross-sectional view of the flow cell shown in FIG. 7.

Further, an example of a specific structure for the flow cell 10 is shown in FIGS. 7 and 8. In this structure, the flow cell block 12 is equipped with the truncated cone shaped sample chamber 11, one window 13 is arranged on each axial end of the flow cell block 12 via a TEFLON® (polytetrafluoroethylene) sheet (gasket) 34, one window flange 14 is arranged on the outside of each window 13 via an O-ring 26, and by fastening the window flange 14 to the flow cell block 12 with screws 35, all the elements can be fastened together in a sealed state. In this regard, although FIGS. 7 and 8 only show this arrangement for one side (the light entrance side in FIG. 8), the other side (the light exit side in FIG. 8) has the same arrangement (except for the central opening which has a different diameter), but it is of course possible to use a different arrangement for the elements on the other side of the flow cell block 12. One specific example of possible dimensions for the sample chamber 11 include a light entrance diameter of 2.1 mm, a light exit diameter of 0.8 mm, and a window spacing of 10.0 mm for the windows 13, 13. Of course, the present embodiment is not limited to these dimensions, but it should be noted that this specific example is one preferred set of dimensions.

Further, a groove 36 is formed in the flow cell block 12 around the surface which makes contact with the sheet 34 so as to face an outer circumferential portion of the sheet 34. The reason for providing the groove 36 is as follows. Namely, in the case where no groove is provided, a reliable liquid-tight and gas-tight seal can be obtained, but it is very difficult to break such seal when the sheet 34 is to be removed. However, in the case of the present embodiment, because the flow cell block 12 is provided with the groove 36, the sheet 34 can be removed easily by pressing a portion of the sheet 34 directly above the groove 36 with a screwdriver or the like. When this is done, the pressed portion of the sheet 34 will sink into the groove 36, and this will cause the portion of the sheet 34 opposite the pressed portion to be pushed up. Then, because the seal between the sheet 34 and the flow cell block 12 is broken, by grasping the pushed up portion of the sheet 34 with fingers, for example, and the sheet 34 can be removed easily. It is for this purpose that the groove 36 is provided in the present embodiment.

Figure 9:
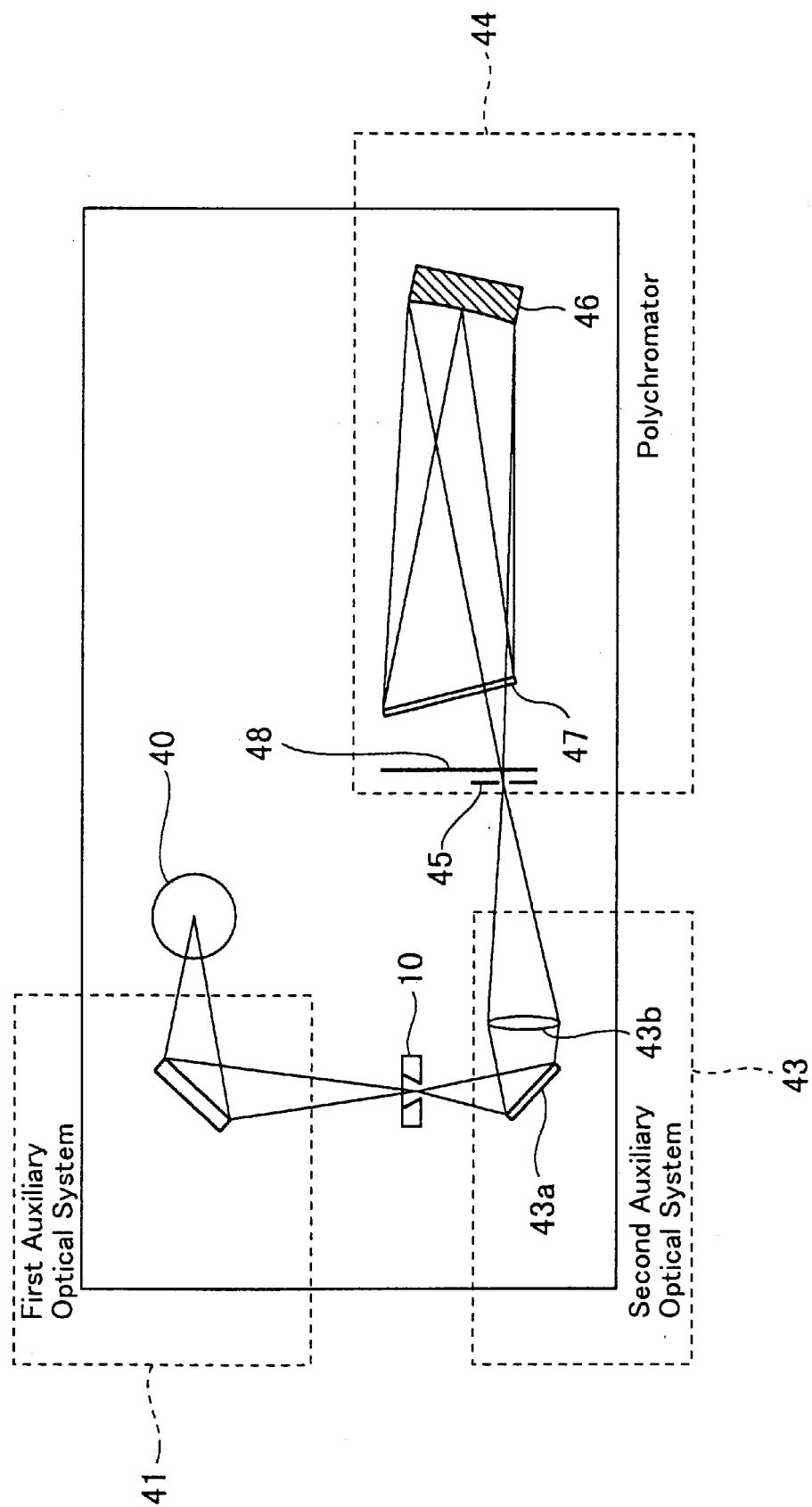
FIG. 9 is a plan view of another embodiment of a detector according to the present invention.
Figure 10:
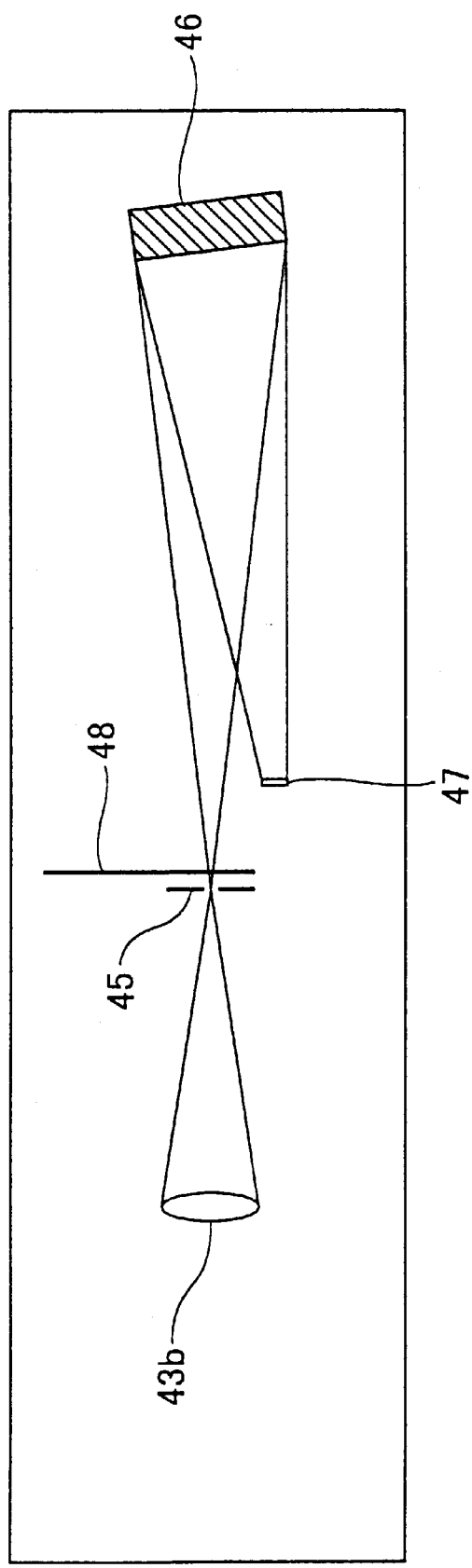
FIG. 10 is a side view of the detector shown in FIG. 9.

Next, FIGS. 9 and 10 show a second embodiment of a multiple wavelength detector according to the present invention. This embodiment has an optical system different than that of the embodiment shown in FIG. 5 and is designed to be more compact. Further, only the deuterium lamp 40 is used as a light source, but depending on the wavelength used, it is possible to use a halogen lamp instead, or or both can be provided with a means for switching between the two. Now, in this arrangement, light from the lamp 40 forms an image at the light exit side of the opening of the flow cell 10 by means of a first auxiliary optical system (e.g., an aspheric mirror) 41.

Next, the light that passes through the flow cell 10 forms an image on an entrance slit 45 of a polychromator 44 by means of a second auxiliary optical system 43 comprised of a plane mirror 43a and a lens 43b arranged after the flow cell 10. Then, the light that passes through the entrance slit 45 is dispersed by a diffraction grating 46 and forms a spectrum on a light detector 47 made from a photodiode array or the like. Further, the entrance side of the polychromator 44 is provided with a shutter 48 driven by a solenoid or a motor, and by operating the shutter 48, it is possible to block the light path. Thus, when necessary, the shutter 48 can be closed to measure the background signals of the optical and electrical systems. In this connection, in the present embodiment, a first optical system is formed from the first auxiliary optical system, and a second optical system is formed from the second auxiliary optical system and the optical system inside the polychromator 44.

Further, these optical systems are formed by applying the technology of not changing the image forming distance of the diffracted light in accordance with wavelength used in the single wavelength UV detector disclosed in Japanese Laid-Open Utility Model Application No. HEI-7-54824 to a multiple wavelength Uw detector, and instead of being arranged on the incident optical path plane, the dispersion direction of the diffraction grating 46 is arranged at an angle from the incident light path plane. In this arrangement, because the surface of the diffraction grating 46 faces a direction roughly aligned with the incident optical axis, it is possible to disperse light having a rather large solid angle without having to use a diffraction grating having large dimensions in the sideways direction. Moreover, it is possible to reduce the dimensions of the polychromator 44 in the sideways direction.

Further, because the light detector (photodiode array) 47 is arranged in a different optical plane than that of the incident light, the portions of light which reflect off the side walls of the polychromator 44 lying in the optical plane of the incident light inside the polychromator 44, the shutter 48 and other structures does not reach the light detector 47, and as a result, stray light in the optical system is reduced. Thus, in the case where this arrangement is used as an absorbance detector, an even larger linear dynamic range is achieved.

Experimental Results

A flow cell was constructed in accordance with the present invention, and then the photodiode array output and the change in the base line of such flow cell was compared with that of a cylindrical flow cell for the case where the solvent is changed. In this experiment, measurement conditions such as wavelength, solvent and the like were as follows, with the light that enters each flow cell forming an image at the light exit side thereof.

First, when each flow cell was filled with $H_2O$, the output of the light detector (photodiode array) at 250 nm and 400 nm was as follows.

TABLE 1

| Wavelength | 250 nm | 400 nm |
|---|---|---|
| Present Invention Flow Cell | 4.3 V | 2.6 V |
| Comparative Example: Cylindrical Flow Cell | 3.4 V | 2.2 V |

Namely, compared to the prior art flow cell, the flow cell according to the present invention allowed the passage of light having 1.3 times as much energy at 250 nm, and 1.2 times as much energy at 400 nm. Furthermore, in the case of the prior art cylindrical flow cell, it was considered that slight changes in the output of the light detector occured depending on where the focal point of the light was positioned. In this regard, the values shown in Table 1 for the prior art cylindrical flow cell are for the case where an image is formed at the light exit side in the same manner as is done in the case of the flow cell according to the present invention.

Next, Table 2 shows the changes in the base line for the case where the solvent is changed.

TABLE 2

| Wavelength: | 250 nm |
|---|---|
| Flow Rate: | 1.0 ml/min |
| Solvent Conditions | |
| 0~10 min: | 100% $H_2O$ |
| 10~20 min: | 100% $H_2O$ → linearly changed to 100% $CH_3CN$ |
| 20~30 min: | 100% $CH_3CN$ |

Figure 11:
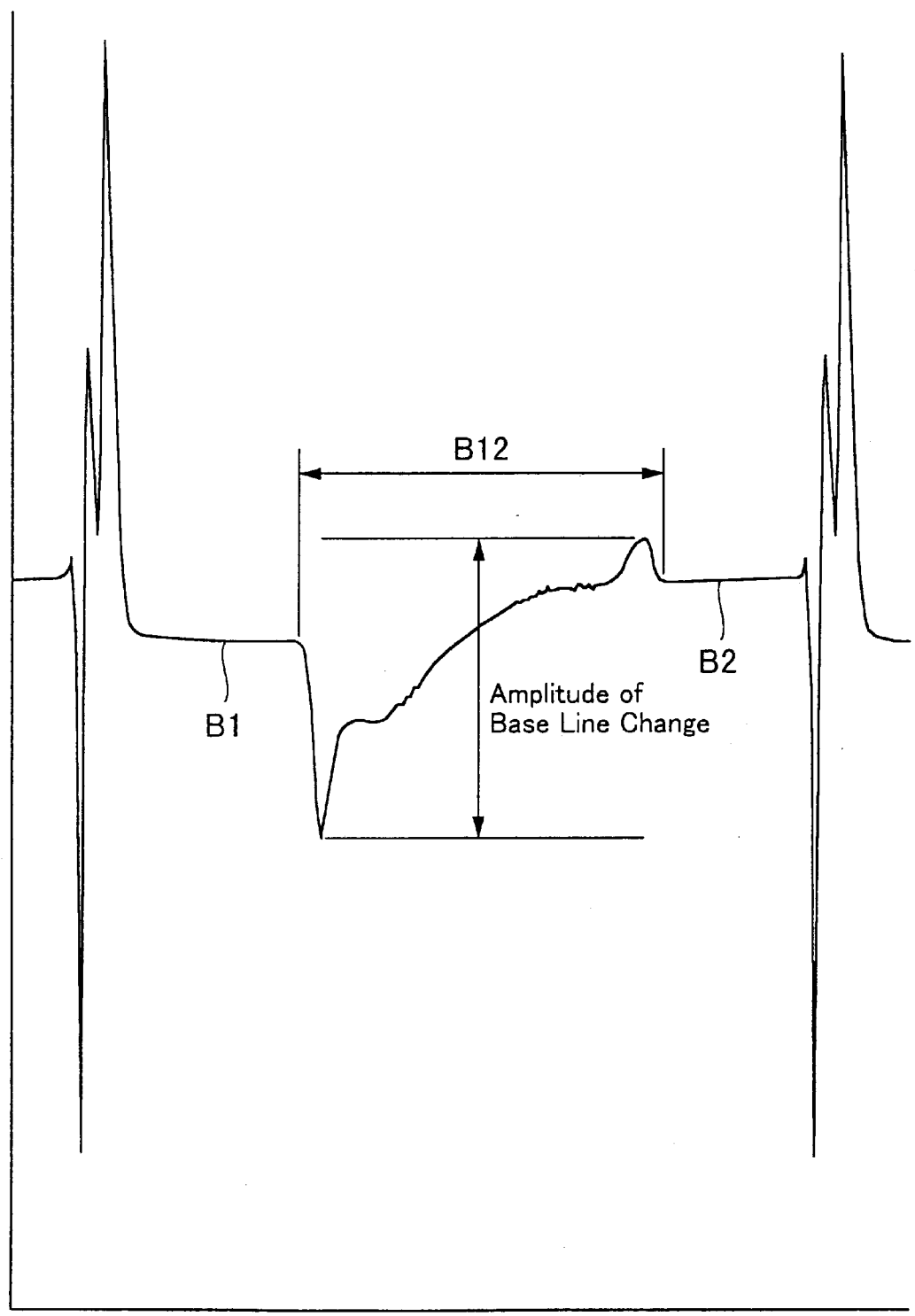
FIG. 11 is a graph showing the measurement results obtained by using a prior art flow cell.
Figure 12:
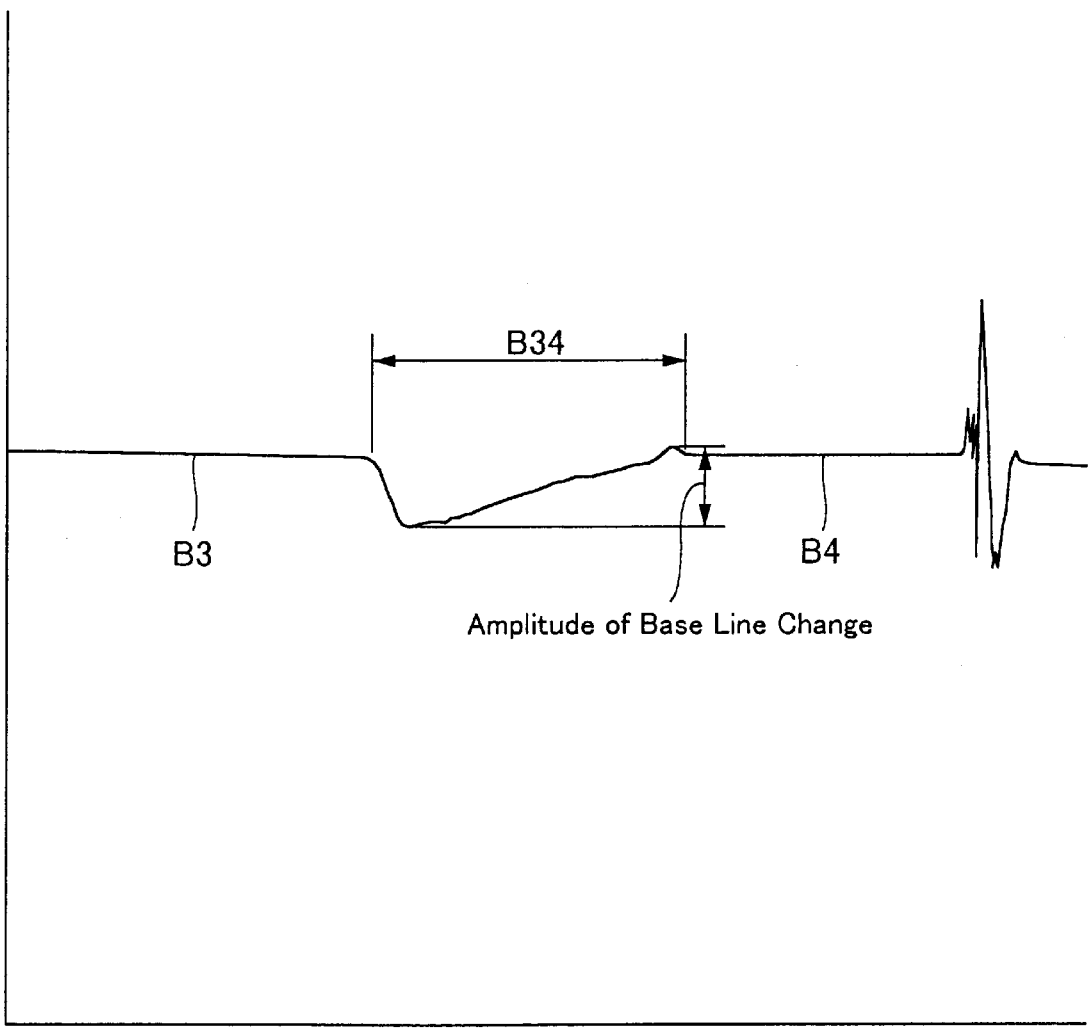
FIG. 12 is a graph showing the measurement results obtained by using a flow cell according to the present invention.

Further, FIG. 11 shows the change in the base line of the flow cell provided with a prior art cylindrical sample chamber for the solvent conditions described above, and FIG. 12 shows the change in the base line of the flow cell according to the present invention for the same conditions. In the graphs shown in FIGS. 11 and 12, the base line for the time when only $H_2O$ is flowing is represented by B1 in FIG. 11 and B3 in FIG. 12, the base line for the time when only $CH_3CN$ is flowing is represented by B2 in FIG. 11 and B4 in FIG. 12, and the time when the base line changes over the gradient ($H_2O→CH_3CN$) is represented by B12 in FIG. 11 and B34 in FIG. 12. From these graphs, the following two points are immediately apparent.

(1) The amplitude of the base line change B34 (represented by the vertical double-headed arrow in the graph) of the flow cell according to the present invention is smaller than the amplitude of the base line change B12 of the prior art flow cell.

(2) The base line shift B3→B4 of the flow cell according to the present invention is small, while the base line shift B1→B2 of the prior art flow cell is large.

Figure 1:
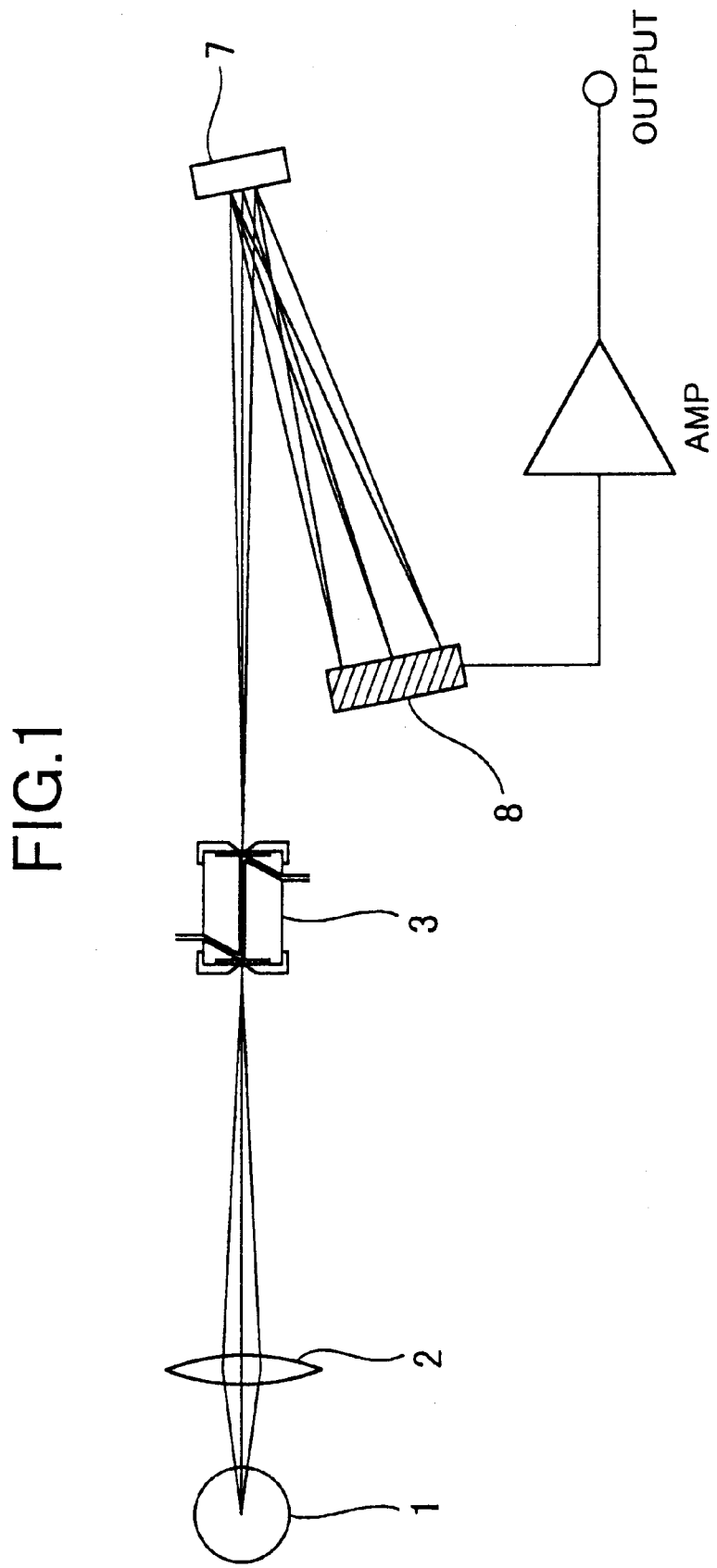
FIG. 1 shows an example of a prior art multiple wavelength detector.
Figure 2:
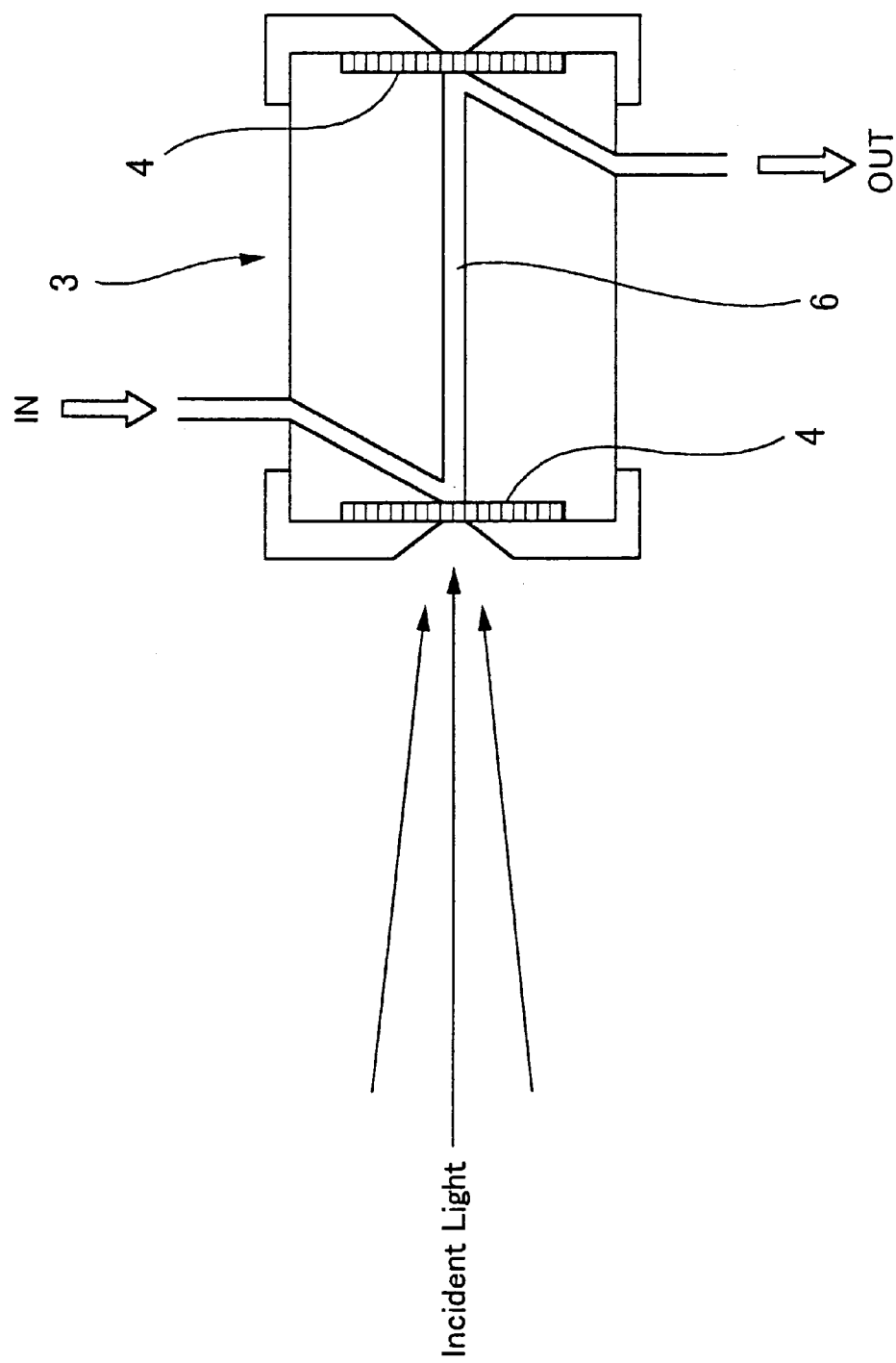
FIG. 2 is an enlarged view of the prior art flow cell shown in FIG. 1.
Figure 3:
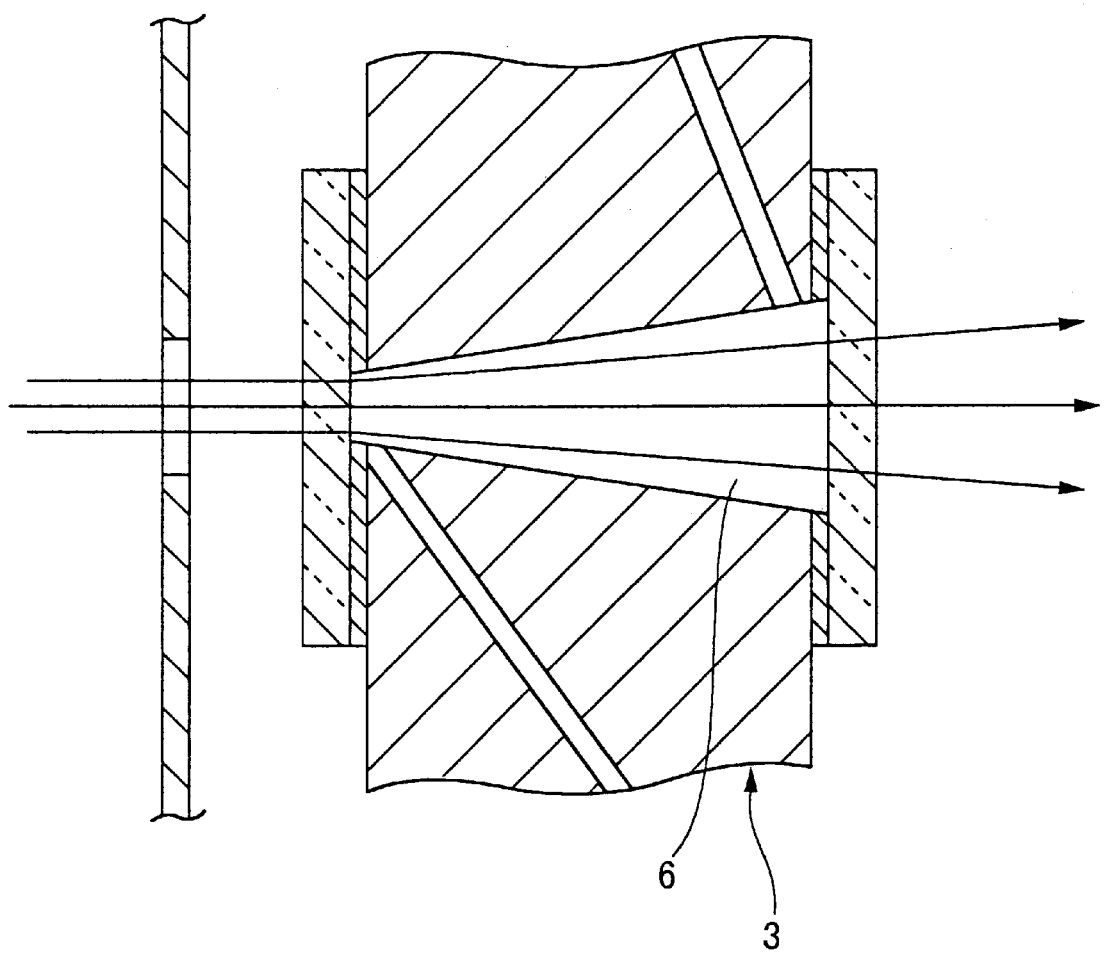
FIG. 3 shows another prior art flow cell.
Figure 13:
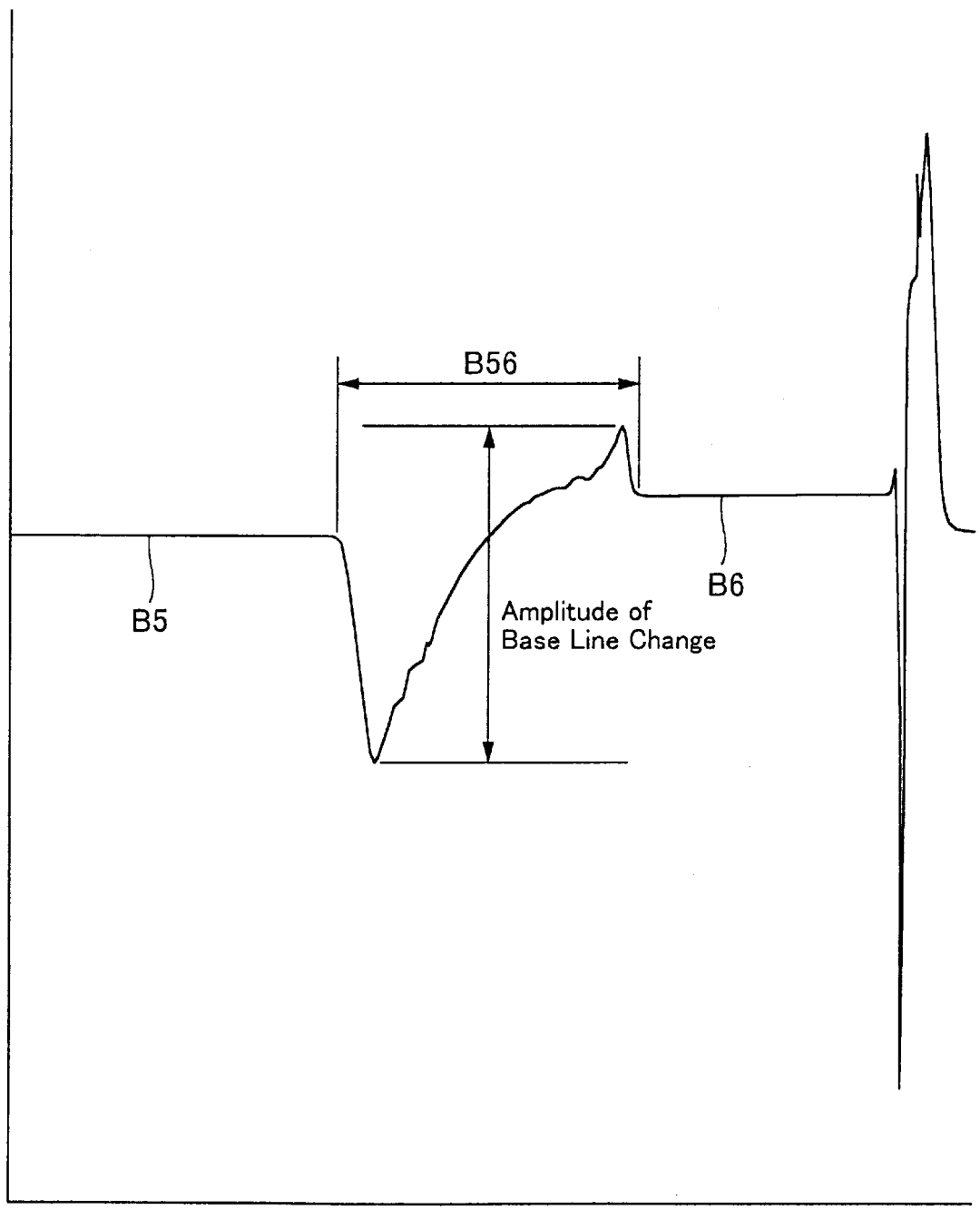
FIG. 13 is a graph showing the measurement results obtained by using another prior art flow cell.

Further, FIG. 13 shows the change in the base line of a flow cell provided with the sample chamber shown in FIG. 3 (i.e., a sample chamber shaped like a truncated cone with the base of such truncated cone positioned at the light exit side of the flow cell). In this graph, the base line for the time when only $H_2O$ is flowing is represented by B5, the base line for the time when only $CH_3CN$ is flowing is represented by B6, and the time when the base line changes over the gradient ($H_2O→CH_3CN$) is represented by B56. From this graph and the graph in FIG. 12, the following two points are immediately apparent.

(1) The amplitude of the base line change B34 (represented by the vertical double-headed arrow in the graph) of the flow cell according to the present invention is smaller than the amplitude of the base line change B56 of the prior art flow cell having the sample chamber shown in FIG. 3.

(2) The base line shift B3→B4 of the flow cell according to the present invention is small, while the height of the base line shift B5→B6 of the prior art flow cell having the sample chamber shown in FIG. 3 is large.

From the experimental results described above, it is clear that in the case where the solvent composition is changed, the base line shift of the flow cell according to the present invention is significantly smaller than the base lines of the prior art flow cell having a cylindrical sample chamber and the prior art flow cell having a truncated cone shaped sample chamber with the base thereof positioned at the light exit side, and this confirms the improvement in base line stability achieved with the flow cell according to the present invention.

Thus, when the flow cell according to the present invention is used in a multiple wavelength detector for liquid chromatography, a larger amount of energy can be utilized than in the case where a prior art flow cell is used. Moreover, because the flow cell according to the present invention minimizes changes in the base line due to changes in the solvent composition, it becomes possible to carry out highly stable measurements.

Figure 14:
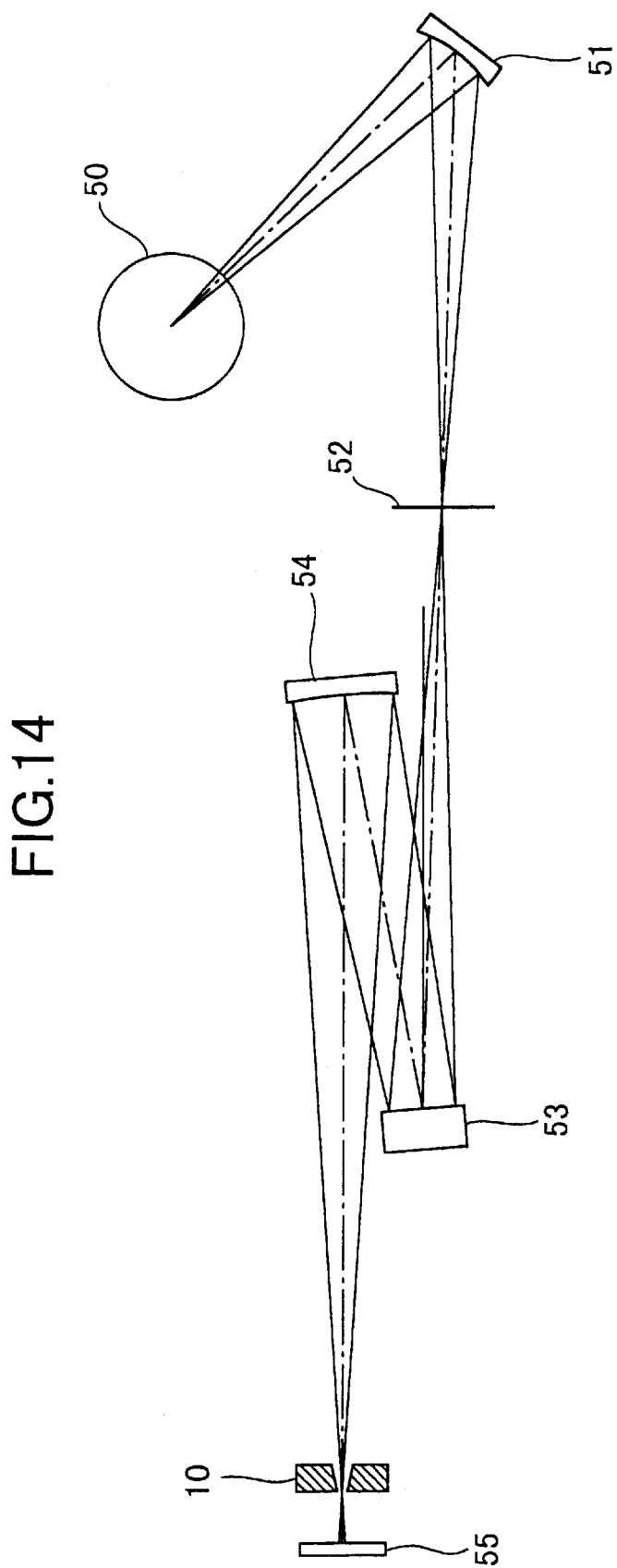
FIG. 14 is a plan view of another embodiment of a detector according to the present invention.

Further, even though each of the embodiments described above was shown as being applied to a multiple wavelength detector, the present invention is not limited to such application, and it is possible to apply the present invention to a single wavelength type UV detector in which monochromatic light is shone through a sample. For example, it is possible to use the arrangement shown in FIG. 14, in which light emitted from a light source 50 is shone into the flow cell 10 by means of a first optical system comprised of a spherical mirror 51, a slit 52, a diffraction grating 53 and a spherical mirror 54. In this way, by providing the diffraction grating 53 as a dispersion element in the first optical system, the light is wavelength dispersed, with only the desired wavelength being passed through the flow cell 10. Further, photodiodes 55 are arranged after the flow cell 10.

Figure 15:
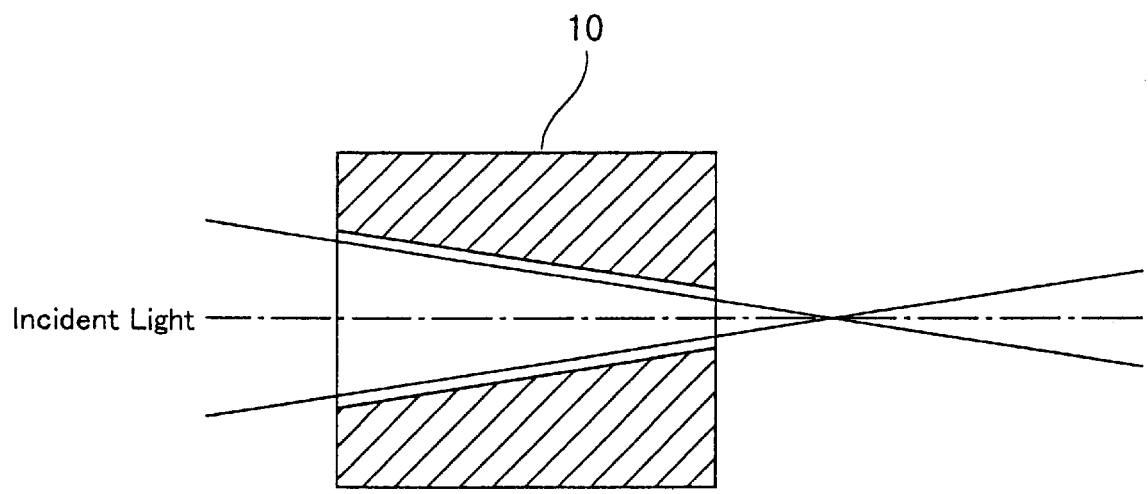
FIG. 15 is a simple drawing showing the relationship between the flow cell and the image forming position of the incident light.

Further, even though in each of the embodiments above the light entering the flow cell 10 was described as forming an image at the light exit side thereof the present invention is not limited to this arrangement, and as shown in FIG. 15, the light may form an image outside the flow cell 10 away from the light exit side. In this case, the elements should be arranged to give the light beam passing through the flow cell 10 a diameter smaller than that of the opening at the light exit side in order to prevent light from being absorbed by the flow cell 10.

Figure 16:
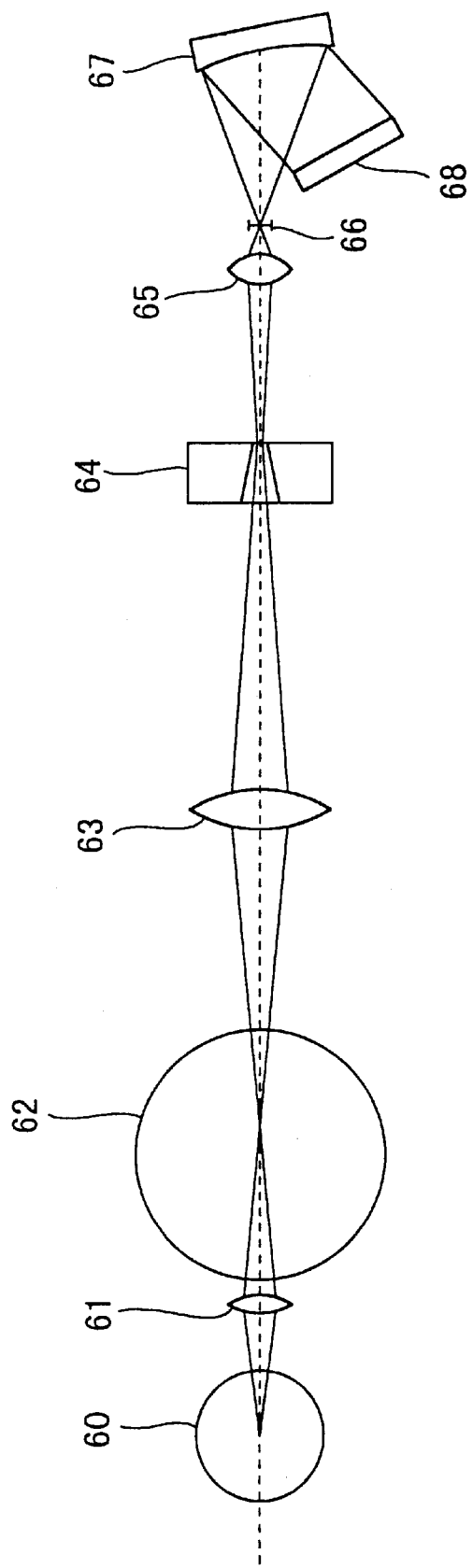
FIG. 16 is a plan view of another embodiment of a detector according to the present invention.

Moreover, it is possible to apply the present invention to detectors of the type shown in FIG. 16, in which light emitted from a tungsten lamp 60 is focused by a lens 61 into a see-through type deuterium lamp 62. In this way, the light from the tungsten lamp 60 combines with the light from the deuterium lamp 62, and this combined light shines out from the deuterium lamp 62. Next, such combined light is focused by a lens 63 to form an image at the light exit side of a flow cell 64. In this regard, the flow cell 64 also uses a truncated cone shaped sample chamber having the structure described above, in which the base of the truncated cone is positioned at the light entrance side of the flow cell 64. Further, the light which passes through the flow cell 64 is converged by a lens 65 to form an image on a slit 66, and after passing through the slit 66, the light is wavelength dispersed by a diffraction grating 67, with such dispersed light being detected by a light detector 68. Now, as is made clear from the drawing, except for the light detector 68, all the elements are arranged linearly. Further, in order to achieve a higher wavelength resolving power and utilization efficiency for the light, the optical elements are so arranged that the distance between the lens 65 and the slit 66 is shorter than that between the light exit side of the flow cell 64 and the lens 65, and this makes it possible to increase the utilization efficiency of the light.

As described above, in the UV detector for liquid chromatography according to the present invention, by providing a truncated cone shaped sample chamber in the flow cell with the base of the truncated cone positioned at the light entrance side of the flow cell, and by arranging elements to focus the light entering the flow cell at a position roughly at the light exit side of the flow cell or a position away from the light exit side, it becomes possible to obtain a large solid angle, whereby the utilization efficiency of the light entering the flow cell is increased, and even in the case where the index of refraction of the solvent flowing through the flow cell changes, it is possible to significantly reduce changes in the base line.

What is claimed is:

1. A UV detector for liquid chromatography, comprising:

a light source;

a flow cell having a light entrance side and a light exit side;

a first optical system for shining light from the light source into the flow cell so as to form an image roughly at the light exit side of the flow cell or a position outside the flow cell at a prescribed distance away from the light exit side thereof;

a light detector;

a second optical system for directing light exiting the flow cell to the light detector; and a truncated cone shaped sample chamber having a large diameter end and a small diameter end and formed in the flow cell along the axial direction thereof, the sample chamber being arranged with the large diameter end of the truncated cone positioned at the light entrance side of the flow cell and operative to permit liquid in the flow cell to flow from the small diameter end of the truncated cone shaped sample chamber toward the large diameter end of said cone shaped sample chamber.

2. The UV detector for liquid chromatography according to claim 1, wherein the second optical system is provided with a dispersion element to enable multiple wavelength measurements.

3. The UV detector for liquid chromatography according to claim 1, wherein the dispersion element is a polychromator.

* * * * *